US006150156A

United States Patent [19]
Riazuddin

[11] Patent Number: 6,150,156
[45] Date of Patent: Nov. 21, 2000

[54] *BACILLUS THURINGIENSIS* ISOLATES ACTIVE AGAINST SUCKING INSECTS

[75] Inventor: Sheikh Riazuddin, Lahore, Pakistan

[73] Assignee: Calgene, Inc., Davis, Calif.

[21] Appl. No.: 09/021,234

[22] Filed: Feb. 10, 1998

Related U.S. Application Data

[60] Provisional application No. 60/040,243, Feb. 11, 1997.

[51] Int. Cl.[7] .............................. C12N 1/20; G01N 33/53; A61K 39/07; A61K 39/02

[52] U.S. Cl. .................. 435/252.31; 435/7.2; 424/246.1; 424/93.461; 424/832; 530/825; 530/810

[58] Field of Search ................................ 435/7.2, 252.31; 424/246.1, 93.461, 832; 530/825, 810

[56] References Cited

FOREIGN PATENT DOCUMENTS

WO 94/04684   3/1994   WIPO .............................. C12N 15/32
WO94/04684    3/1994   WIPO .

*Primary Examiner*—Hankyel Park
*Attorney, Agent, or Firm*—Calgene, Inc.; Timothy K. Ball; Dennis R. Hoerner, Jr.

[57] ABSTRACT

The subject invention concerns novel *Bacillus thuringiensis* strains containing parasporal proteins with pesticidal properties against whitefly, aphid, jassid, and possibly other sucking insects of agronomic importance, and peptide sequences to these proteins that can be used to obtain structural genes. The spores or crystals of these microbes, or mutants thereof, are useful to control hymenopteran pests in various environments. The genes of the invention can be used to transform various hosts wherein the novel toxic proteins can be expressed.

5 Claims, No Drawings

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(30)
<223> OTHER INFORMATION: "w" represents either an A or T nucleotide

<400> SEQUENCE: 1
tcwacwaaaa cwaatgtwgt wgaagtwctw                                    30

<210> SEQ ID NO 2
<211> LENGTH: 24
<212> TYPE: PRT
<213> ORGANISM: Bacillus thuringiensis
<220> FEATURE:
<221> NAME/KEY: VARIANT
<222> LOCATION: (1)...(24)
<223> OTHER INFORMATION: Xaa = Any Amino Acid

<400> SEQUENCE: 2

Xaa Pro Lys Thr Asn Val Val Glu Val Leu Asn Lys Xaa Val Ala Asn
 1               5                  10                  15

Trp Asn Xaa Leu Tyr Val Phe Leu
            20

<210> SEQ ID NO 3
<211> LENGTH: 10
<212> TYPE: PRT
<213> ORGANISM: Bacillus thuringiensis

<400> SEQUENCE: 3

Ser Thr Lys Thr Asn Val Val Glu Val Leu
 1               5                  10

BACILLUS THURINGIENSIS ISOLATES ACTIVE AGAINST SUCKING INSECTS

CROSS REFERENCE TO RELATED APPLICATIONS

This application claims the benefit of U.S. Provisional Application Ser. No. 60/040,243, filed, Feb. 11, 1997.

FIELD OF THE INVENTION

This invention relates to *Bacillus thuringiensis* isolates containing parasporal proteins with pesticidal properties against whitefly, aphid, jassid and other sucking insects of agronomic importance. More specifically, the invention relates to the novel *Bacillus thuringiensis* proteins and compositions and methods for expressing the active insecticidal *Bacillus thuringiensis* proteins in a host cell.

BACKGROUND OF THE INVENTION

Control of agricultural pests has relied mainly on the use of chemical insecticides. The use of such man-made insecticide presents a number of technical and social issues that include a) development of insect resistance in the field, b) threat to beneficial microbial flora in the soil, c) human health hazards, and d) increase in the environmental burden.

*Bacillus thuringiensis* (Bt) is a gram positive ubiquitous soil bacterium characterized by its ability to produce crystalline inclusions during sporulation. The ingested Bt crystal protein is hydrolyzed to an active toxic molecule that binds covalently to the brush border membrane vesicles of the target larvae leading to creation of holes in the gut and/or osmotic imbalance with eventual death of the larvae. There is a high degree of host specificity for the various Bt pesticidal proteins, and to date no adverse effect on mammals including human beings/beneficial microbial flora has been reported. For these reasons, Bt has been considered a positive and effective alternative to chemical insecticides for many applications.

Problems can arise as new insect pests become endemic, however, or as existing populations develop resistance to a particular level or type of *Bacillus thuringiensis* toxin. *Bacillus thuringiensis* has been shown to be effective predominantly but not exclusively against Lepidopteran, Dipteran, and Coleopteran larvae. Cry proteins (d-endotoxins) from *Bacillus thuringiensis* have potent insecticidal activity against a number of these insects. These proteins are classified CryI to CryV based on amino acid sequence homology and insecticidal activity.

Most CryI proteins are synthesized as protoxins (ca. 130–140 kDa) then solubilized and proteolytically processed into active toxin fragments (ca. 60–70 kDa).

A large number of agronomically important pests are from the Lepidopteran, Dipteran, and Coleopteran insects. Sucking insects, however, present an important alternate class of pests that destroy host plants, not only through direct invasion but also as carriers of devastating viruses which are transferred into the host plant when the insect sucks fluid from the plant phloem. For example, whitefly (*Bemisia tabaci*) damages cotton plants by direct invasion and is also the carrier of leaf-curl virus, which attacked cotton in Sudan in the 1980's and in Pakistan in the early 1990's.

To date there are no known chemicals/biological agents that can effectively control the spread and infection of plant viruses, and for this reason there is a continuing need for new methods to control the virus vectors and virus carriers. Recently, some reports have extended the host range of Bt to nematodes, fleas, cockroach, and aphids (1994 U.S. Pat. Nos. 05,350,577; 05,322,932; 05,281,530; 05,378,460; 05,350,5576; 05,302,387; 05,350,5576; and PCT/U.S. 93/07409). Despite the existence of these reports, few applications for using Bt have been developed other than for use against Lepidopteran, Dipteran, and Coleopteran larvae.

For all of these reasons, there is a particular need for new forms of the *Bacillus thuringiensis* toxin for use in protecting plants, a need which will only increase with time. More particularly, there is a continuing need to introduce newly discovered or alternative *Bacillus thuringiensis* genes into crop plants.

SUMMARY OF THE INVENTION

The subject invention concerns novel, newly discovered isolates of *Bacillus thuringiensis* that have pesticidal properties against sucking insects, i.e., against whitefly, aphid, jassid, and other sucking insects of agronomic importance. Using the newly discovered Bt isolates as source materials, pesticidal proteins have been purified and partially sequenced to obtain information that can be used a) to transform suitable microbial hosts to develop into Bt pesticide, b) transform host plants to breed resistance against sucking insects thus reducing the damages caused by viruses carried by the insects.

The subject invention is additionally drawn to genes that encode novel proteins active against sucking insects. The novel Bt isolates, described herein as CAMB 786, CAMB 787, CAMB 788, CAMB 789, and CAMB 3616, have been shown to be active against both whiteflies and aphids, while CAMB 3667 is so far known to be active against whiteflies. The activity of CAMB 3667 against aphids has not yet been determined.

The subject invention also encompasses mutants of the above isolates that have substantially the same pesticidal properties as the parent isolate. Procedures for making mutants are well known in the microbiological art. Ultraviolet light, nitrosoguanidine, site specific changes in DNA bases, and random molecular and chemical libraries are used extensively toward this end.

DETAILED DESCRIPTION OF THE INVENTION

This invention provides five new isolates of *Bacillus thuringiensis*. These samples were collected as part of an overall program to make a search for new and novel Bt isolates/pesticidal genes in samples collected from different ecological environments in Pakistan. The cultures disclosed in this application were deposited Feb. 11, 1997, with the American Type Culture (12301 Parklawn Drive, Rockville, Md. 20852) Collection as ATCC Accession Nos. 55930 (*Bacillus thuringiensis* CAMB 786); 55931 (*B. thuringiensis* CAMB 787); 55932 (*B. thuringiensis* CAMB 788); 55933 (*B. thuringiensis* CAMB 789); 55934 (*B. thuringiensis* CAMB 3616); and 55935 (*B. thuringiensis* CAMB 3667).

The Bt isolates of the invention can be cultured using standard methods known in the art, including known media and fermentation techniques. Upon completion of the fermentation techniques, the bacteria can be harvested by first separating the Bt spores and crystals from the fermentation broth by means well known in the art. The recovered Bt spores and crystals can be formulated into a wettable powder, liquid concentrate, granules, or other formulations by the addition of surfactants, dispersants, inert carriers, and other components to facilitate handling and application for particular target pests. These formulation and application procedures are all well known in the art.

Formulated products can be applied as baits to control sucking insect pests. The Bt cells of the invention can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Methods for such treatment and chemical reagents are well known to the art.

Information from sequence analysis data is used to construct oligos that are used as probes in the isolation and identification of the structural genes of the said proteins. Genes encoding toxins having activity against the target susceptible pests can be isolated from the Bt isolate of the invention by use of well known procedures.

Methods are available in the art for the identification and isolation of the protein or proteins associated with insecticidal activity. Generally, proteins can be purified by conventional chromatography as well as other separation techniques. Chromatographic methods include gel-filtration, ion-exchange, and immunoaffinity chromatography; high-performance liquid chromatography, such as reversed-phase, ion-exchange, size-exclusion, chromatofocusing, and hydrophobic interaction chromatography, etc. Electrophoretic separation techniques include methods such as one-dimensional gel electrophoresis, two-dimensional gel electrophoresis, etc.

Such methods are known in the art. See for example *Current Protocols in Molecular Biology*, Vols. 1 and 2, Ausubel et al. (eds.), John Wiley & Sons, NY (1988).

Additionally, antibodies can be prepared against substantially pure preparations of proteins. See, for example, Radka et al. (1983) *J. Immunol.* 128:2804; and Radka et al. (1984) *Immunogenetics* 19:63. Any combination of methods may be utilized to purify proteins having insecticidal properties, particularly activity against sucking insects. As the protocol is being formulated, insecticidal activity is determined after each purification step.

Such purification steps will result in a substantially purified protein fraction. By "substantially purified" or "substantially pure" is intended protein that is substantially free of any components associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase, or capillary electrophoresis. The terms "substantially pure" or "substantially purified" are not meant to exclude artificial or synthetic mixtures of the proteins with other compounds. The terms are also not meant to exclude the presence of minor impurities that do not interfere with the biological activity of the protein, and which may be present, for example, due to incomplete purification.

Substantially purified proteins can be characterized and sequenced by standard methods known in the art. The purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides can be separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized and can be used as a probe to aid in the isolation of the gene encoding the pesticidal protein.

Once the purified protein has been isolated and characterized, it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the proteins that show activity against sucking insects as well as components and fragments thereof. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the insecticidal protein. However, after each change, and particularly when it is difficult to predict the exact effect of the substitution, deletion, or insertion, one skilled in the art will appreciate that the effect will be evaluated by routine screening assays.

The proteins or other component polypeptides described herein may be used alone or in combination. That is, several proteins may be used to control different insect pests. Further, the proteins may be used in combination with other insecticidal principles. Other Bt δ-endotoxins are known in the art.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones that express an active pesticidal protein can be sequenced to determine the nucleotide sequence of the gene. Then, an amino acid sequence can be deduced for the protein. For general molecular methods, see, for example, *Molecular Cloning: A Laboratory Manual*, Second Edition, Vols. 1–3, Sambrook et al. (eds.), Cold Spring Harbor Laboratory Press, Plainview, N.Y. (1989), and the references cited therein.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example, EPA 0359472; EPA 0385962; WO 91/16432; Perlak et al. (1991) *Proc. Natl. Acad. Sci. USA* 88:3324–3328; and Murray et al. (1989) *Nucleic Acids Research* 17:477–498. In this manner, the genes can be synthesized utilizing plant preferred codons. That is the preferred codon for a particular host is the single codon that most frequently encodes that amino acid in that host. The maize preferred codon, for example, for a particular amino acid may be derived from known gene sequences from maize. See, Murray et al. (1989) *Nucleic Acids Research* 17:477–498. Synthetic genes can also be made based on the distribution of codons a particular host uses for a particular amino acid. In this manner, the nucleotide sequences can be optimized for expression in any plant. It is recognized that all or any part of the gene sequence may be optimized or synthetic. That is, synthetic or partially optimized sequences may also be used.

A wide variety of ways are available for introducing a Bt gene expressing a toxin into a microorganism host under conditions that allow for stable maintenance and expression in the gene. These methods are well known to those skilled in the art. Also well known are methods for using the transformed host cells, or extracts thereof, in applying the Bt toxin gene to control insect pests. See, for example, PCT Application WE 94/04684.

In developing expression constructs for use in plants, various fragments comprising the regulatory regions and open reading frame may be subjected to different processing conditions, such as ligation, restriction enzyme digestion, PCR, in vitro mutagenesis, and in vitro synthesis to optimize codon usage, linkers and adapters addition, and the like. Thus, nucleotide transitions, transversions, insertions, deletions, or the like, may be performed on the DNA that is employed in the regulatory regions or the DNA sequences of interest for expression in the plant, particularly the plastids and/or plant phloem. Methods for restriction digests, Klenow blunt end treatments, ligations, and the like are well known to those in the art and are described, for example, by Maniatis et al. (in *Molecular Cloning: a laboratory manual* (1982) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA, or manipulation of the DNA by joining or removing sequences, linkers, or the like. Preferably, the vectors will be capable of replication to at least a relatively high copy number in *E. coli*. A number of vectors are readily available for cloning, including such vectors as pBR322, vectors of the pUC series, the M13 series vectors, and pBluescript vectors (Stratagene; La Jolla, Calif.).

In order to provide a means of selecting the desired plant cells, vectors for plastid transformation typically contain a construct that provides for expression of a selectable marker gene. Marker genes are plant-expressible DNA sequences that express a polypeptide that resists a natural inhibition by, attenuates, or inactivates a selective substance, i.e., antibiotic, herbicide, etc.

Alternatively, a marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes or identification, i.e., they will be distinguishable from nontransformed cells. The characteristic phenotype allows the identification of cells, cell groups, tissues, organs, plant parts, or whole plants containing the construct.

Detection of the marker phenotype makes possible the selection of cells having a second gene to which the marker gene has been linked. This second gene typically comprises a desirable phenotype that is not readily identifiable in transformed cells, but that is present when the plant cell or derivative thereof is grown to maturity, even under conditions wherein the selectable marker phenotype itself is not apparent.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310–6314 (bromoxynil resistance nitrilase gene); and Sathasivan et al. (1990) *Nucl. Acids Res.* 18:2188 (AHAS imidazolinone resistance gene).

Where transformation and regeneration methods have been adapted for a given plant species, either by Agrobacterium-mediated transformation, bombardment, or some other method, the established techniques may be modified for use in selection and regeneration methods to produce plastid-transformed plants.

For example, the methods described herein for tobacco are readily adaptable to other solanaceous species, such as tomato, petunia, and potato.

In Brassica, Agrobacterium-mediated transformation and regeneration protocols generally involve the use of hypocotyl tissue, a nongreen tissue which might contain a low plastid content. Thus, for Brassica, preferred target tissues would include microspore-derived hypocotyl or cotyledonary tissues (which are green and thus contain numerous plastids) or leaf tissue explants. While the regeneration rates from such tissues may be low, positional effects, such as seen with Agrobacterium-mediated transformation, are not expected, thus it would not be necessary to screen numerous successfully transformed plants in order to obtain a desired phenotype.

For cotton, transformation of *Gossypium hirsutum* L. cotyledons by cocultivation with *Agrobacterium tumefaciens* has been described by Firoozabady et al., (1987) *Plant Mol. Biol.* 10: 105–116 and Umbeck et al., (1987) *Bio/Technology* 5:263–266. Again, as for Brassica, this tissue may contain insufficient plastid content for chloroplast transformation. Thus, as for Brassica, an alternative method for transformation and regeneration of alternative target tissue containing chloroplasts may be desirable, for instance targeting green embryogenic tissue.

Other plant species may be similarly transformed using related techniques. Alternatively, microprojectile bombardment method, such as described by Klein et al. (*Bio/Technology* 10:286–291) may also be used to obtain nuclear transformed plants comprising the viral single subunit RNA polymerase expression constructs described herein. Cotton transformation by particle bombardment is reported in WO 92/15675, published Sep. 17, 1992.

Stable transformation of tobacco plastid genomes by particle bombardment is reported in Svab et al. (1990) *Proc. Natl. Acad. Sci. USA* 87:8526–8530 and Svab and Maliga (1993) *EMBO J.* 12:601–606. U.S. Pat. No. 5,576,198 describes a method for controlled expression by directing the plant to express protein in plastids of specific tissues, at specific times or in response to specific induction. Transformation of plastids for expression of Bt toxin proteins in the plastid organelle is described in U.S. Pat. No. 5,545,818. The methods described therein may be employed to obtain plants transformed for expression of the Bt protein of this invention.

The Bacillus strains of the invention may be used for protecting agricultural crops and products from sucking pests. Alternatively, a gene encoding the toxins of the invention may be introduced via a suitable vector into a microbial host, and said host applied to the environment or plants. Microorganism hosts that are known to occupy the phytosphere of one or more crops of interest may be selected. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

A number of ways are available for introducing a gene expressing the pesticidal protein into the microorganism host under conditions that allow for stable maintenance and expression of the gene. Such methods are readily available in the art. Generally, expression cassettes can be constructed so as to include the DNA constructs of interest operably linked with the transcriptional and translational regulatory signals for expression of the DNA constructs, and a DNA sequence homologous with a sequence in the host organism, whereby integration will occur, and/or a replication system that is functional in the host, whereby integration or stable maintenance will occur. See, for example, U.S. Pat. No. 5,039,523; U.S. Pat. No. 4,853,331; EPO 0480762A2; Sambrook et al. supra; *Molecular Cloning: A Laboratory Manual*, Maniatis et al. (eds.) Cold Spring Harbor Laboratory, Cold Spring Harbor, N.Y. (1982); *Advanced Bacterial Genetics*, Davis et al. (eds.) Cold Spring Harbor Laboratory, Cold Spring Harbor, N.Y. (1980); and the references cited therein.

General methods for employing the strains of the invention in pesticide control or in engineering other organisms as pesticidal agents are known in the art. See, for example, U.S. Pat. No. 5,039,523 and EP 0480762A2.

The Bacillus strains of the invention or the microorganisms that have been genetically altered to contain the insecticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides, or mixtures of several of these preparations, if desired, together with further agriculturally acceptable carriers, surfactants, or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders, or fertilizers.

The invention now being generally described, it will be more readily understood by reference to the following examples, which are included for purposes of illustration only and are not intended to limit the present invention.

EXAMPLES

Following are examples that illustrate procedures, including the best mode, for practicing the invention. These examples should not be construed as limiting. All percentages are by weight and all solvent mixture proportions are by volume unless otherwise noted.

Example 1

Characterization of Bt Isolates

A subculture of the Bt isolate can be used to inoculate a peptone, glucose, salts medium, and the Bt spores and crystals, can be obtained and isolated by procedures well known in the art. The novel *Bacillus thuringiensis* isolates of the subject invention have the following characteristics in their biologically pure form:

Table-1: Bt Isolates Characteristics

Characteristics of Bt CAMB 786

Colony morphology: round, whitish, dull appearance, margin with uniform spikes, typical for Bt.

Culture method: T3 medium (Travers et al. (1987) *Appl. Environ. Microbiol* 53(6):1263–1266, typical for Bt.

Inclusion: very small oval-shaped crystals, abundant.

Approximate molecular weight of alkali-soluble, trypsin activated major proteins: 55, and 65 kDa.

Characteristics of Bt CAMB 787

Colony morphology: whitish, dull appearance with undulate margin, typical for Bt.

Culture method: T3 medium, typical for Bt.

Inclusion: very small oval-shaped crystals, not abundant.

Approximate molecular weight of alkali-soluble, trypsin activated major proteins: 40, and 60 kDa.

Characteristics of Bt CAMB 788

Colony morphology: round, whitish, dull appearance, margin with uniform spikes, typical for Bt.

Culture method: T3 medium, typical for Bt.

Inclusion: very small oval-shaped crystals, not abundant.

Approximate molecular weight of alkali-soluble, trypsin activated major proteins: 40, and 60 kDa.

Characteristics of Bt CAMB 789

Colony morphology: round, whitish, dull appearance with undulate margin, typical for Bt.

Culture method: T3 medium, typical for Bt.

Inclusion: very small oval-shaped crystals, abundant.

Approximate molecular weight of alkali-soluble, trypsin activated major proteins: 50 kDa.

Characteristics of Bt CAMB 3616

Colony morphology: whitish, a bit glossy appearance with undulate margin, typical for Bt.

Culture method: T3 medium, typical for Bt.

Inclusion: very small oval-shaped crystals, not abundant.

Approximate molecular weight of alkali-soluble, trypsin activated major proteins: 39 kDa.

Characteristics of Bt CAMB 3667

Colony morphology: whitish, a bit glossy appearance, margin with uniform spikes, typical for Bt.

Culture method: T3 medium, typical for Bt.

Inclusion: oval-shaped crystals, not abundant.

Approximate molecular weight of alkali-soluble, trypsin activated major proteins: 50, 65, 100 kDa.

The subject Bt isolates were picked up for their uncharacteristic protein profile of SDS-PAGE gel and non-homology to the known cry genes during processing of the collected samples.

Example 2

Crude Extracts

Bt isolates were grown for 72 hours to sporulation, harvested by centrifugation, and the cell mass including bacterial spores and protein crystals were solubilized in alkaline buffer at pH 10.00 and finally treated with trypsin at a concentration of 5%. The crude extract was tested both for bioactivity against different insects and run on native SDS-PAGE gel before and after trypsin treatment. Table-2 gives the bioactivity spectrum of the various proteins.

Example 3

Activity

TABLE-2

Bt ACTIVITY AGAINST SUCKING INSECTS

| Bt Identification | Activity (LC50 ng/μl) | |
|---|---|---|
| | Aphid | White fly |
| CAMB 786 (SEQ ID NO: 1) | 62 | 52.8 |
| CAMB 787 (SEQ ID NO: 3) | 328 | 250 |
| CAMB 788 | 114 | 250 |
| CAMB 789 | 196 | 146 |
| CAMB 3616 | 83 | 128 |
| CAMB 3667 | 204 | 52 |

Example 4

Protein Purification and sequencing

Bt crude protein extract was purified by 2-D gel electrophores is, or molecular sieve chromatography. Proteins were eluted from the gel, transferred to PVDF membrane by using spin blot cartridges. The PVDF immobilized proteins were microsequenced. N-terminal amino acid sequences were determined by the standard Edman reaction with an automated gas-phase sequenator (App lied Biosystems, Inc.).

The sequences obtained were,

| | |
|---|---|
| CAMB 786 | M/G P K T N V V E V L N K - V A N W N - L Y V F L |
| CAMB 787 | S T K T N V V E V L |
| CAMB 788 | Not Determined |
| CAMB 789 | Not Determined |
| CAMB 3616 | Not Determined |
| CAMB 3667 | Not Determined |

Example 5

Preparation of oligo DNAs and cloning

From these sequencing data oligonucleotide probes were designed by utilizing a codon frequency table assembled from available sequence data from other Bt toxin genes. The probes were synthesized on an Applied Biosystems, Inc., DNA synthesis machine.

Total cellular DNA was prepared by growing CAMB 786 Bt cells to a low optical density in SPY medium (Kronstad et al. (1984) *J. Bacteriol.* 160:95–102) and harvesting the cells by centrifugation. The cells were lysed by the usual methods, the cellular debris precipitated overnight at 4° C. at 100 mM neutral salt, and the supernatant was extracted twice with phenol/chloroform (1:1). The DNA was precipitated with ethanol and purified by Cesium Chloride density gradient. Total cellular DNA was digested from BamHI and HindIII restriction enzymes and separated by electrophoresis on a 0.8% agarose-TAE (50 mM Tris HCl, 20 mM NaOAc, 2.5 mM EDTA, pH 8.0) buffered gel. Southern blot of the gel was hybridized with a $^{32}$P radiolabeled oligonucleotide probe derived from the N-terminal amino acid sequence of purified 55 kDa protein from CAMB 786. The sequence of the oligonucleotide synthesized is 5' TCT/A ACT/A AAA ACT/A AAT GTT/A GTT/A GAA GTT/A CTT/A 3'. The result shows the hybridizing fragments of approximately 6 Kb from BamHI digest and 3 Kb from HindIII digest presumptively identifying the gene.

Example 6

Insertion of Toxin Gene into Plants

One aspect of the subject invention is the transformation of plants with genes coding for pesticidal genes against whitefly and/or aphid. The transformed plants will be resistant to attack by whitefly and/or aphid.

Genes coding for whitefly toxins, as described herein, can be inserted into plant cells using a variety of techniques that are well known in the art. If promoters specific for expression in plant phloem were used, the expression can be targeted into the sucking insect food from the plant.

All publications, patents, and patent applications mentioned in this specification are indicative of the level of skill of those skilled in the art to which this invention pertains. All publications and patent applications are herein incorporated by reference to the same extent as if each individual publication or patent application is specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A method for controlling pests from the family Aphididae which comprises contacting said pests with an aphid-controlling amount of a *Bacillus thuringiensis* isolate selected from the group consisting of Bt CAMB 786, Bt CAMB 787, Bt CAMB 788, Bt CAMB 3616, and Bt CAMB 3667, and variants thereof, or toxic crystals or spores of said isolates.

2. A composition of matter comprising *Bacillus thuringiensis* selected from any one of the group consisting of Bt CAMB 786, Bt CAMB 787, Bt CAMB 788, Bt CAMB 3616, and Bt CAMB 3667 or mutants thereof, or spores or crystals of any one of said Bt in association with an insecticide carrier.

3. A biologically pure culture of *Bacillus thuringiensis* selected from the group consisting of Bt CAMB 786, Bt CAMB 787, Bt CAMB 788, Bt CAMB 3616, and Bt CAMB 3667, and variants thereof.

4. A toxin that is active against hymenopteran pests and that is producible by a *Bacillus thuringiensis* selected from the group consisting of Bt CAMB 786, Bt CAMB 787, Bt CAMB 788, Bt CAMB 3616, and Bt CAMB 3667, and variants thereof.

5. A method for controlling sucking insects, which comprises administering to said insects or to their environment, a composition, culture, or toxin according to any of claims 2 to 4.

* * * * *